(12) United States Patent
Honda et al.

(10) Patent No.: US 11,701,164 B2
(45) Date of Patent: Jul. 18, 2023

(54) ENERGY TREATMENT SYSTEM AND OUTPUT CONTROL METHOD THEREOF

(71) Applicant: OLYMPUS CORPORATION, Hachioji (JP)

(72) Inventors: Satoshi Honda, Hachioji (JP); Tsuyoshi Hayashida, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 917 days.

(21) Appl. No.: 16/298,124

(22) Filed: Mar. 11, 2019

(65) Prior Publication Data

US 2019/0201076 A1 Jul. 4, 2019

Related U.S. Application Data

(63) Continuation of application No. PCT/JP2016/076975, filed on Sep. 13, 2016.

(51) Int. Cl.
*A61B 18/12* (2006.01)
*A61B 17/32* (2006.01)
*A61B 18/00* (2006.01)

(52) U.S. Cl.
CPC .......... *A61B 18/1233* (2013.01); *A61B 17/32* (2013.01); *A61B 18/12* (2013.01);
(Continued)

(58) Field of Classification Search
CPC ............ A61B 2018/00994; A61B 2018/00708
See application file for complete search history.

(56) References Cited

U.S. PATENT DOCUMENTS 10,842,563 B2 * 11/2020 Gilbert ............... A61B 18/1206
2002/0156466 A1 * 10/2002 Sakurai ............... A61B 1/00016
606/1

(Continued)

FOREIGN PATENT DOCUMENTS

CN 102209502 A 10/2011
CN 103826561 A 5/2014
(Continued)

OTHER PUBLICATIONS

Dec. 13, 2016 International Search Report issued in International Patent Application No. PCT/JP2016/076975.
(Continued)

*Primary Examiner* — Thomas A Giuliani
*Assistant Examiner* — Christine A Dedoulis
(74) *Attorney, Agent, or Firm* — Oliff PLC

(57) ABSTRACT

An energy treatment system and a output control method thereof according to embodiments of the present invention perform treatment by energy supply in which ultrasonic energy and high frequency energy are combined, stop or suppress discharge by reducing the output of high frequency energy within a set period when a state in which discharge is likely to occur during treatment is detected, and change the output of ultrasonic energy. In addition, in order for a user to continue treatment without feeling uncomfortable and to ensure incision performance, each output is controlled so that the set period is as short as possible or is supplemented, and also, the set period expires, and control is performed so as to reduce the possibility of discharge even at the time of returning.

13 Claims, 8 Drawing Sheets

(52) U.S. Cl.
CPC ............ *A61B 2018/00607* (2013.01); *A61B 2018/00642* (2013.01); *A61B 2018/00678* (2013.01); *A61B 2018/00708* (2013.01); *A61B 2018/00779* (2013.01); *A61B 2018/00994* (2013.01)

(56) References Cited

U.S. PATENT DOCUMENTS

| | | | |
|---|---|---|---|
| 2008/0125768 A1* | 5/2008 | Tahara | A61B 18/1206 606/34 |
| 2009/0254080 A1* | 10/2009 | Honda | A61B 18/1402 606/38 |
| 2010/0145332 A1* | 6/2010 | Shibata | A61B 18/148 606/41 |
| 2012/0165816 A1 | 6/2012 | Kersten et al. | |
| 2013/0190660 A1* | 7/2013 | Tanaka | A61B 18/1402 601/2 |
| 2014/0276754 A1 | 9/2014 | Gilbert et al. | |
| 2016/0287317 A1 | 10/2016 | Tsubuku et al. | |

FOREIGN PATENT DOCUMENTS

| | | |
|---|---|---|
| CN | 104042335 A | 9/2014 |
| JP | 2013-504396 A | 2/2013 |
| WO | 2010/064530 A1 | 6/2010 |
| WO | 2013/042498 A1 | 3/2013 |
| WO | 2015/122307 A1 | 8/2015 |

OTHER PUBLICATIONS

Dec. 3, 2020 Office Action issued in Chinese Patent Application No. 201680089264.6.

May 30, 2017 Office Action issued in Japanese Application No. 2017-521178.

Mar. 19, 2019 International Preliminary Report on Patentability issued in International Application No. PCT/JP2016/076975.

* cited by examiner

ENERGY TREATMENT SYSTEM AND OUTPUT CONTROL METHOD THEREOF

CROSS-REFERENCE TO RELATED APPLICATIONS

This application is a Continuation Application of PCT Application No. PCT/JP2016/076975, filed Sep. 13, 2016, the entire contents of which are incorporated herein by reference.

BACKGROUND OF THE INVENTION

1. Field of the Invention Field

The present invention relates to an energy treatment system for outputting a combination of ultrasonic energy and high frequency energy to a treatment subject site and performing treatment, and an output control method thereof.

2. Description of the Related Art

Generally, a high frequency treatment instrument using a high frequency output and an ultrasonic treatment instrument using an ultrasonic output are known as apparatuses which perform treatment such as incision and coagulation on a treatment subject site such as a biological tissue. In addition, Patent Literature 1: Jpn. PCT National Publication No. 2013-504396 proposes an example of an energy treatment instrument which performs treatment by combining an ultrasonic output and a high frequency output.

The above-described energy treatment instrument can simultaneously perform Incision and coagulation by simultaneously outputting an ultrasonic output (ultrasonic energy) and a high frequency output (high frequency energy) to a treatment subject site via a treatment unit provided at the tip, thereby performing treatment more smoothly. On the other hand, mist due to the ultrasonic output diffuses, but it is necessary to suppress a discharge so that the mist does not come in contact with the discharge.

When the high frequency output becomes excessive during the treatment, the state becomes easy to discharge. Therefore, the discharge can be prevented by providing an interruption period in which the supply of the high frequency output is interrupted. On the other hand, since the treatment is performed only by the ultrasonic output during the interruption period, the incision performance of the treatment instrument is deteriorated and the operator lacks the smoothness of the incision, thus giving a sense of incompatibility during the treatment.

Therefore, the present invention provides an energy treatment system and an output control method thereof, which perform treatment by outputting a combination of ultrasonic energy and high frequency energy, detect an abnormal state in which discharge is likely to occur during treatment, and control high frequency energy and ultrasonic energy so as to minimize the deterioration of incision performance.

BRIEF SUMMARY OF THE INVENTION

According to an embodiment of the present invention, there is provided an energy treatment system comprising: an energy treatment instrument which performs treatment on a subject by simultaneously using ultrasonic energy and high frequency energy; an ultrasonic energy generator which supplies the ultrasonic energy to the energy treatment instrument; a high frequency energy generator which supplies the high frequency energy to the energy treatment instrument; an excessive output detector which compares a parameter obtained from the output of the high frequency energy with a reference parameter obtained from the output of the high frequency energy in the case of not being in an abnormal state, detects whether the output of the high frequency energy is an excessive output, and outputs an abnormality signal when the excessive output is detected; and a high frequency energy controller which stops the output of the high frequency energy or reduces the output of the high frequency energy from an output of the high frequency energy at steady state during a preset set period when the abnormality signal is outputted by the excessive output detector.

Further, according to an embodiment of the present invention, there is provide an operating method of an energy generation apparatus, the operating method comprising: supplying, by an ultrasonic energy generator, ultrasonic energy to an energy treatment instrument; supplying, by a high frequency energy generator, high frequency energy to the energy treatment instrument; comparing, by an excessive output detector, a parameter obtained from the output of the high frequency energy with a reference parameter obtained from the output of the high frequency energy in the case of not being in an abnormal state, detecting whether the output of the high frequency energy is an excessive output, and outputting an abnormality signal when the excessive output is detected; and stopping, by a high frequency energy controller, the output of the high frequency energy or reduces the output of the high frequency energy from an output of the high frequency at steady state during a preset set period when the abnormality signal is outputted by the excessive output detector.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinafter, embodiments of the present invention will be described in detail with reference to the drawings.

Figure 1:
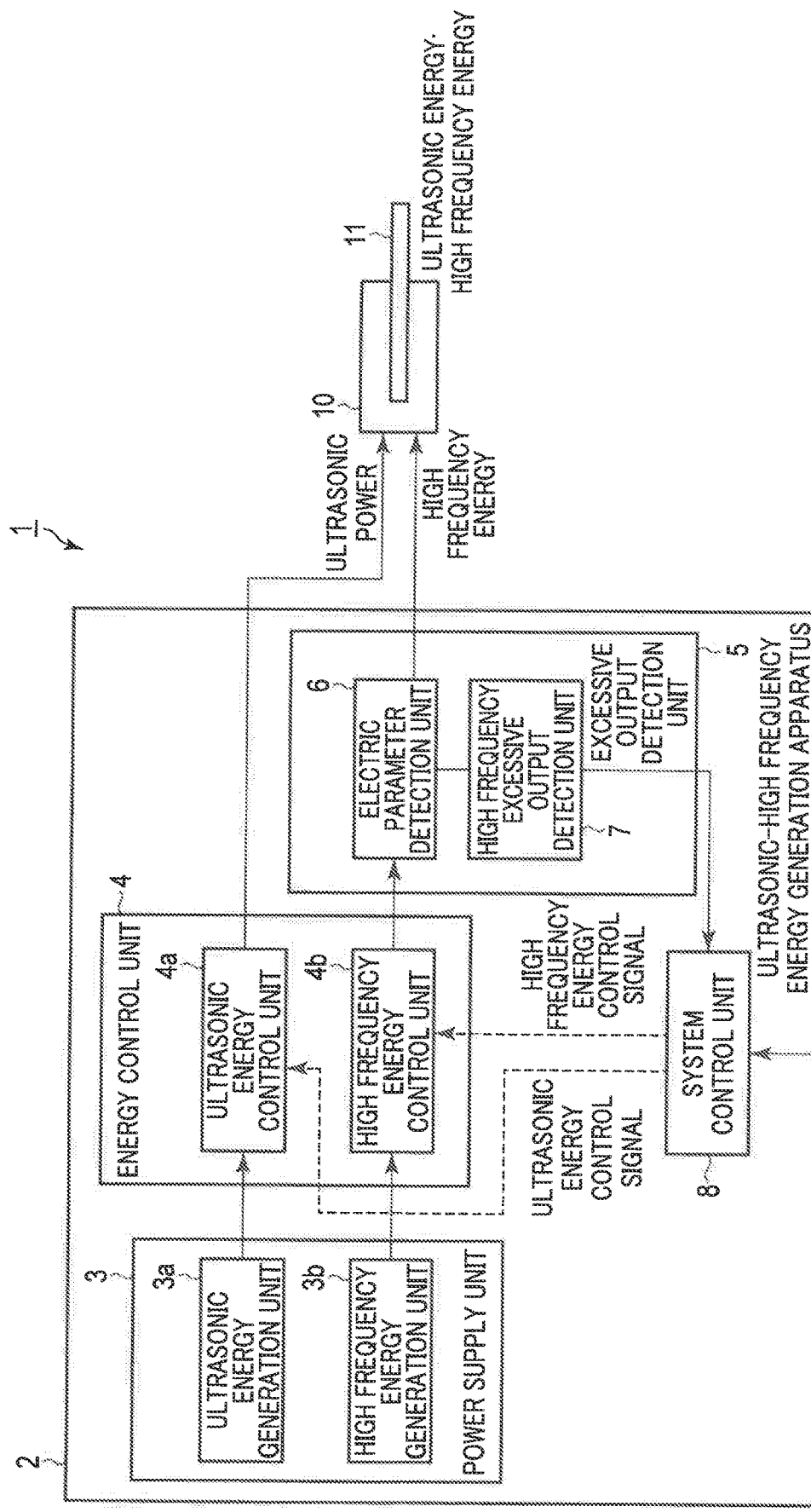
FIG. 1 is a figure showing a conceptual configuration example of an energy treatment system according to the present embodiment.

FIG. 1 is a figure showing a conceptual configuration example of an energy treatment system according to the present embodiment.

The energy treatment system 1 includes an ultrasonic-high frequency energy generation apparatus 2, an operation switch 9, and an energy treatment instrument 10 such as an ultrasonic-high frequency combined handpiece equipped with an ultrasonic vibrator (not shown).

The ultrasonic-high frequency energy generation apparatus 2 includes a power supply unit 3 which generates driving power including high frequency power, an energy control unit (energy controller) 4, an excessive output detection unit (excessive output detector) 5, a system control unit (system controller) 8 including a central processing unit (CPU). This configuration shows only the components capable of realizing the technical features of the present invention, and other commonly provided components such as a display unit are normally provided. In the following description, energy includes electric energy, including high frequency electric power or other driving electric power, and vibration wave energy generated by vibration.

Among them, the power supply unit 3 includes an ultrasonic energy generation unit (ultrasonic energy generator) 3a which generates ultrasonic power for driving an ultrasonic vibrator to generate ultrasonic energy, and a high frequency energy generation unit (high frequency energy generator) 3b which generates high frequency energy (high frequency output).

The energy control unit 4 includes an ultrasonic energy control unit 4a and a high frequency energy control unit 4b. The energy control unit 4 receives a high frequency energy control signal and an ultrasonic energy control signal, described later, from the system control unit 8. The high frequency energy control unit (high frequency energy controller) 4b performs the supply or stop of high frequency energy and performs the increase or decrease of the output value, and the ultrasonic energy control unit (ultrasonic energy controller) 4a performs the supply or stop of ultrasonic power, performs the increase or decrease of the output value, and performs frequency modulation. The energy control unit 4 may be not only a circuit configuration of a switching circuit or the like but also a software control, and has general versatility so that it is possible to appropriately select and execute the rise state of the high frequency energy control signal and the ultrasonic energy in a return period of each output control method described later according to the instruction of the system control unit 8.

The excessive output detection unit 5 includes an electric parameter detection unit (electric parameter detector) 6 and a high frequency excessive output detection unit (high frequency excessive output detector) 7. The electric parameter detection unit 6 detects a voltage value and a current value from the high frequency energy output from the energy control unit 4, and calculates a power value, an impedance value, a resistance value, and the like. A determination of an abnormal state in the excessive output detection unit 5 detects that the possibility of occurrence of discharge increases by comparing a high frequency impedance value as a parameter with a high frequency impedance value acquired under an environment, in which discharge hardly occur, as a reference (reference parameter). Here, although the high frequency impedance value is described as the parameter, it is not particularly limited as long as the abnormal state can be numerically detected. For example, it may be the detected voltage value, current value, and power value.

The high frequency excessive output detection unit 7 detects whether the high frequency energy is in an abnormal state, that is, whether the output is excessive. When it is detected that the output is excessive, an abnormality signal S4 notifying that the possibility of occurrence of discharge due to the high frequency energy has increased is output to the system control unit 8.

In the present embodiment, although the high frequency excessive output detection unit 7 obtains and determines the impedance and outputs the abnormality signal. However, it may be configured so that an abnormal state is determined by comparing a calculated electrical numerical value as a parameter with a preset parameter.

The system control unit 8 receives the abnormality signal S4 from the excessive output detection unit 5, and outputs a high frequency energy control signal and an ultrasonic energy control signal to the energy control unit 4. The system control unit 8 has a function of performing driving control on the other components in the ultrasonic-high frequency energy generation apparatus 2. As will be described later, the energy control unit 4 performs output control such as raising high frequency energy and supplying the increased high frequency energy again after interrupting the high frequency energy during a certain period.

The operation switch 9 is provided on the ultrasonic-high frequency energy generation apparatus 2 side or the energy treatment instrument 10 side and instructs driving of the ultrasonic-high frequency energy generation apparatus 2.

The energy treatment instrument 10 shows a configuration example of a monopolar type in which a probe 11 on a tip side extends from a main body portion in combination with an external electrode (not shown). An ultrasonic vibrator (not shown) is provided in the main body portion. The ultrasonic vibrator generates ultrasonic vibration by supplying ultrasonic power from the ultrasonic energy control unit 4a and outputs the ultrasonic vibration as ultrasonic energy. The energy treatment instrument 10 may be a bipolar type in which a sandwich structure is provided on the tip side of the probe. In the bipolar type, an opening/closing movable jaw is attached to a fixing portion of a probe tip.

[First Output Control Method]

Figure 2:
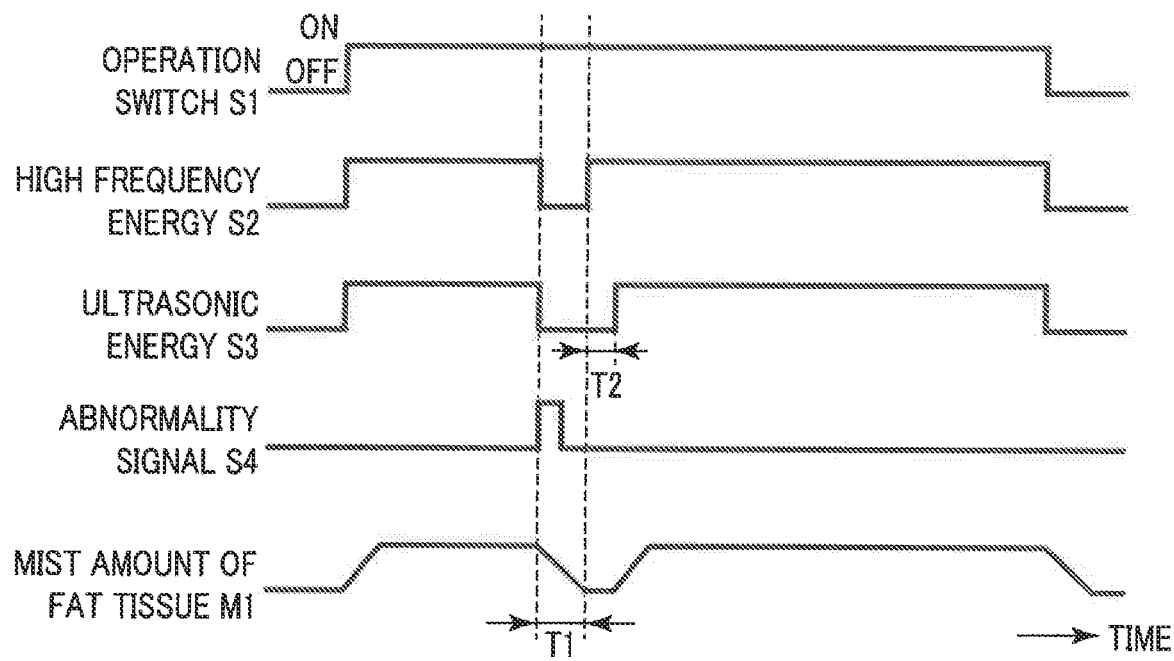
FIG. 2 is a timing chart for explaining a first output control method.

Next, a first output control method when high frequency energy in the energy treatment system 1 is excessive will be described with reference to a timing chart shown in FIG. 2.

When a signal S1 which is an ON signal is input to the system control unit 8 by the ON operation of the operation switch 9, the power supply unit 3 is driven to generate ultrasonic power and high frequency power, respectively, and output the ultrasonic power and the high frequency power to the ultrasonic energy control unit 4a and the high frequency energy control unit 4b of the energy control unit 4. The ultrasonic energy control unit 4a supplies ultrasonic power to the energy treatment instrument 10 and generates ultrasonic energy S3 caused by ultrasonic vibration at the probe tip. In addition, at the same time, the high frequency energy control unit 4b supplies high frequency energy S2 to the energy treatment instrument 10 via the excessive output detection unit 5.

Therefore, the energy treatment instrument 10 simultaneously outputs the high frequency energy S2 and the ultrasonic energy S3, so that the treatment of the treatment subject is performed. According to the progress of the treatment, a fat tissue included in a treatment subject site is generated in the form of mist. The mist includes minute tissue pieces of the fat tissue scraped off by ultrasonic vibration. Therefore, when the treatment with the ultrasonic energy S3 is stopped or reduced, the occurrence of the mist is reduced.

When the excessive output detection unit 5 detects the excessive output of the high frequency energy during the treatment and the abnormality signal S4 is input to system control unit 8, the ultrasonic energy control unit 4a stops the output of the ultrasonic energy S3 according to the instruction of the system control unit 8, and at the same time, the high frequency energy control unit 4b stops the output of the high frequency energy S2 during a predetermined interruption period T1. In the following description, interrupting the output of each energy, that is, stopping the output means setting the output to 0 level or 0 potential (0 V).

The interruption period T1 is previously set as a set period until the remaining mist is sufficiently reduced and the problem does not occur even if the discharge occurs. The interruption period is such a short time that the operator performing the treatment does not notice that the interruption of the high frequency energy output has occurred, and is set to, for example, 100 msec or less and several tens of msec.

After the interruption period T1 ends, the high frequency energy S2 is output. The energy treatment instrument 10 outputs only the high frequency energy S2 at the steady state and resumes the treatment. Further, the output of the ultrasonic energy S3 is resumed with the time difference of the return period T2 delayed from the interruption period T1. Due to such resumption, the energy treatment instrument 10 simultaneously supplies the high frequency energy S2 and the ultrasonic energy S3 to the treatment subject and performs the treatment. Upon completion of the treatment, the operation switch 9 is turned off, and both the outputs of the high frequency energy S2 and the ultrasonic energy S3 are stopped.

As described above, the discharge in the mist can be prevented by providing the interruption period having a short period that interrupts the supply of the high frequency energy S2 and the ultrasonic energy S3 when the high frequency energy becomes excessive. In addition, since the supply of the ultrasonic energy S3 is resumed with the time difference from the resumption of the supply of the high frequency energy S2, overshoot occurs when the supply of the high frequency energy S2 is resumed, and even if the discharge occurs, there is no supply of the ultrasonic energy S3, whereby no mist is present.

[Second Output Control Method]

Figure 3:
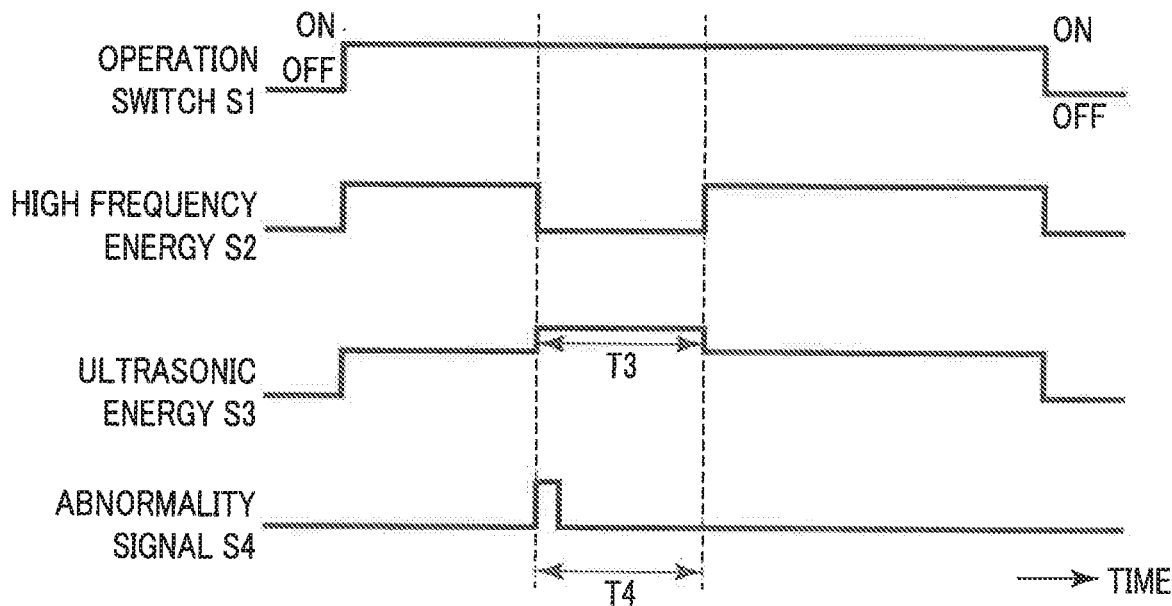
FIG. 3 is a timing chart for explaining a second output control method.

Next, a second output control method when high frequency energy in the energy treatment system 1 is excessive will be described with reference to a timing chart shown in FIG. 3.

As in the first output control method described above, the system control unit 8 drives the power supply unit 3 by the ON operation of the operation switch 9 and generates ultrasonic power and high frequency power. The energy treatment instrument 10 simultaneously outputs high frequency energy S2 and ultrasonic energy S3, so that the treatment of the treatment subject is performed. According to the progress of the treatment, a fat tissue included in a treatment subject site is generated in the form of mist in the vicinity of the probe 11, as described above.

When the excessive output detection unit 5 detects the excessive output of the high frequency energy S2 during the treatment and the abnormality signal S4 is input to system control unit 8, the high frequency energy control unit 4b is stopped so that the output of the high frequency energy S2 is interrupted during a predetermined interruption period T4, according to the instruction of the system control unit 8.

The system control unit 8 stops the output of the high frequency energy S2, transmits an ultrasonic energy control signal for increasing the output to the ultrasonic energy control unit 4a, and increases ultrasonic energy S3 during an output increase period T3. Here, the increase of the ultrasonic energy S3 is to increase an amplitude of an ultrasonic wave. In addition, in the output increase period T3, a time of 100 msec or more is set. Here, as the ultrasonic energy S3 increases, the amount of mist generated increases, but since the output of the high frequency energy S2 is stopped, no discharge occurs.

As an interruption period T4 ends, the system control unit 8 transmits a high frequency energy control signal to the high frequency energy control unit 4b and returns the high frequency energy S2 to an original output value. At the same time, the system control unit 8 transmits an ultrasonic energy control signal to the ultrasonic energy control unit 4a, reduces the ultrasonic energy S3, and returns the ultrasonic energy S3 to an original output value. The energy treatment instrument 10 simultaneously outputs high frequency energy S2 and ultrasonic energy S3, so that the treatment in the steady state is resumed. The output of the high frequency energy S2 and the ultrasonic energy S3 is stopped by the OFF operation of the operation switch 9.

According to the output control method, as in the first output control method described above, since the output of the ultrasonic energy S3 is continuously increased even if the supply of the high frequency energy S2 is stopped according to the detection of the abnormality signal, it is possible to reduce a decrease rate of incision performance in the treatment.

[Third Output Control Method]

Figure 4:
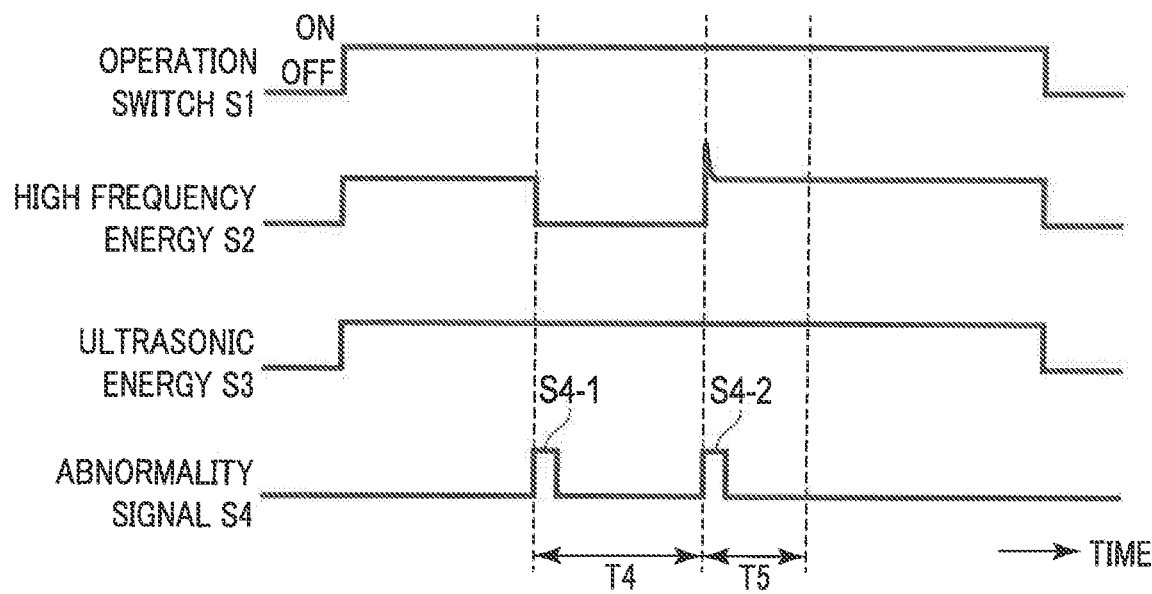
FIG. 4 is a timing chart for explaining a third output control method.

Next, a third output control method when high frequency energy in the energy treatment system is excessive will be described with reference to a timing chart shown in FIG. 4.

As in the first output control method described above, the energy treatment instrument 10 simultaneously outputs high frequency energy S2 and ultrasonic energy S3 by the ON operation of the operation switch 9, so that the treatment of the treatment subject is performed. According to the progress of the treatment, a fat tissue included in a treatment subject site is generated in the form of mist in the vicinity of the probe 11, as described above.

When the excessive output detection unit 5 detects the excessive output of the high frequency energy during the treatment and an abnormality signal S4-1 is input to system control unit 8, the energy control unit 4 causes the high frequency energy control unit 4*b* to stop the output of the high frequency energy S2 during a predetermined interruption period T4 according to the instruction of the system control unit 8. In this example, a return period T5 is provided subsequent to the interruption period T4.

During the return period T5 after the end of the interruption period T4, the system control unit 8 transmits a high frequency energy control signal to the high frequency energy control unit 4*b* and returns the high frequency energy S2 to an original output value. Overshoot may occur when the high frequency energy S2 rises. When the overshoot occurs, an abnormality signal (or detection signal) S4-2 shown in FIG. 4 is more likely to be output from the excessive output detection unit 5, but the system control unit 8 does not respond unnecessarily by invalidating the abnormality signal or reducing the sensitivity.

According to the output control method, as in the first output control method described above, the return period T5 in which the detection is invalid is provided subsequent to the interruption period T4 of the high frequency energy S2 by stopping the supply of the high frequency energy S2 according to the detection of the abnormality signal. Therefore, even if an overshoot occurs when the supply of the high frequency energy S2 is resumed, the system control unit 8 does not respond to the abnormality signal S4-2, and as a result, unnecessary output stop is suppressed.

[Fourth Output Control Method]

Figure 5:
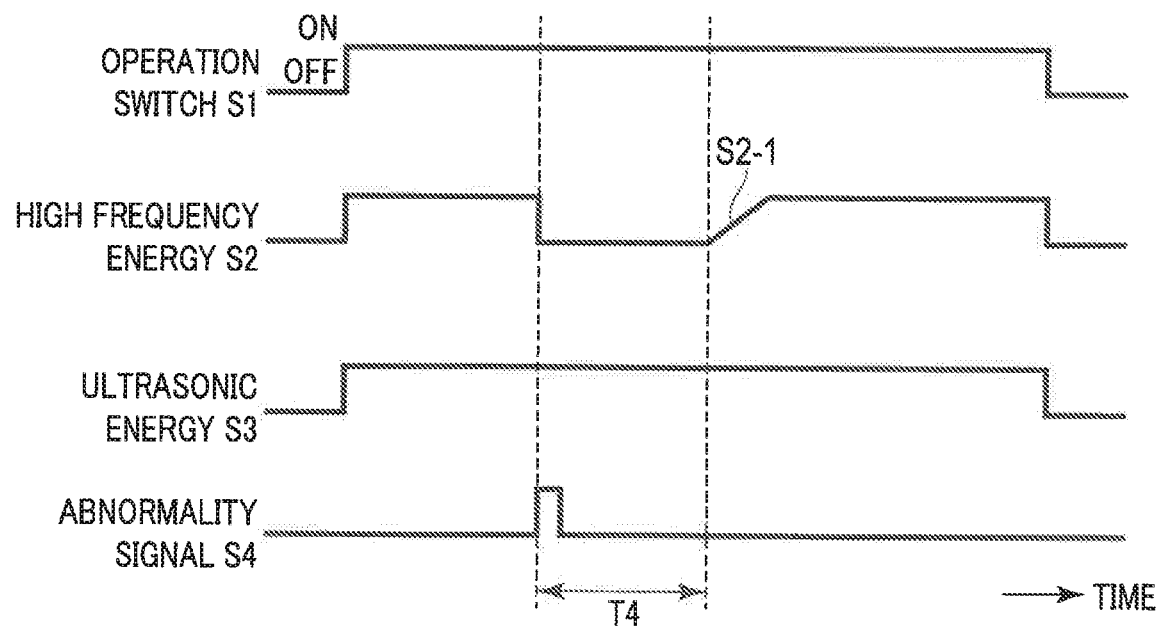
FIG. 5 is a timing chart for explaining a fourth output control method.

Next, a fourth output control method when high frequency energy in the energy treatment system is excessive will be described with reference to a timing chart shown in FIG. 5.

As in the first output control method described above, the energy treatment instrument 10 simultaneously outputs high frequency energy S2 and ultrasonic energy S3, so that the treatment of the treatment subject is performed. According to the progress of the treatment, a fat tissue included in a treatment subject site is generated in the form of mist in the vicinity of the probe 11, as described above.

When the excessive output detection unit 5 detects the excessive output of the high frequency energy S2 during the treatment and the abnormality signal S4 is input to system control unit 8, the high frequency energy control unit 4*b* stops the output of the high frequency energy S2 during a predetermined interruption period T4 according to the instruction of the system control unit 8.

As an interruption period T4 ends, the system control unit 8 transmits a high frequency energy control signal to the high frequency energy control unit 4*b* and returns the high frequency energy S2 to an original output value. The return of the output value is started up in the form of pulses in the above-described output control method. However, in the fourth output control method, when returning to the original output value, the rise of high frequency energy S2-1 has an inclination, gradually rises so as to prevent overshoot, and returns.

According to the output control method, it is possible to prevent the discharge in the mist by stopping the supply of the high frequency energy S2 in the first output control method described above. Further, the occurrence of overshoot can be prevented by increasing the high frequency energy S2 so as to have the inclination when returning the high frequency energy S2, and the occurrence of the abnormality signal due to erroneous detection of the excessive output detection unit 5 can be prevented. The soft start is suitable for a low voltage and power mode or a low CF mode which does not generate spark.

[Fifth Output Control Method]

Figure 6A:
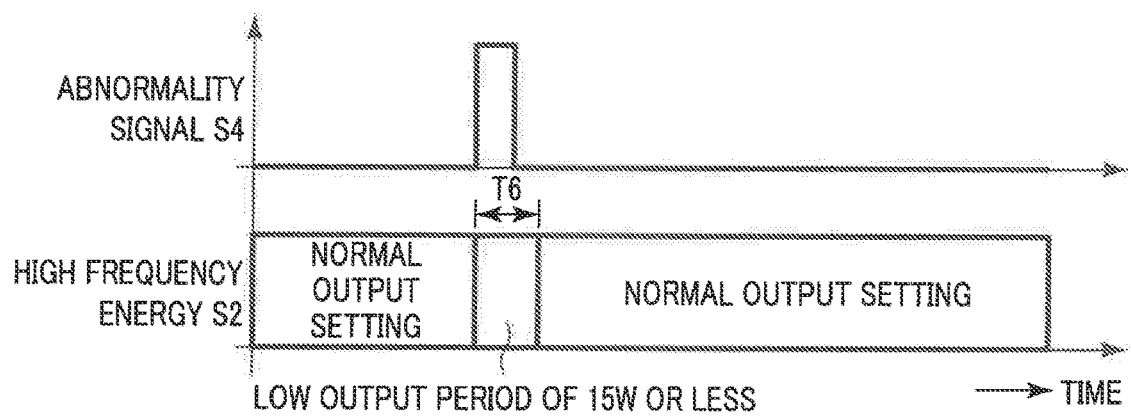
FIG. 6A is a timing chart for explaining a fifth output control method.
Figure 6B:
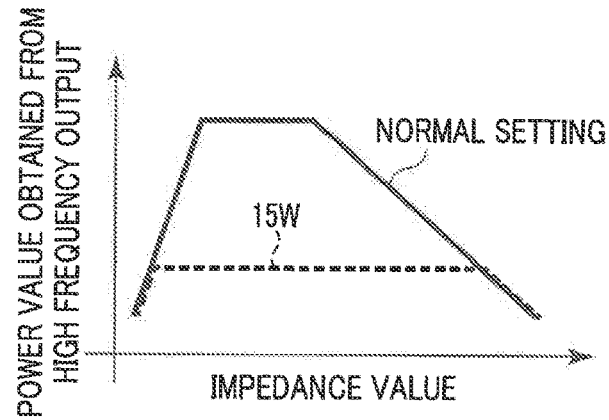
FIG. 6B is a figure showing a relationship between an impedance value and a power value obtained from high frequency energy.

Next, a fifth output control method when high frequency energy in the energy treatment system is excessive will be described with reference to a timing chart shown in FIG. 6A. FIG. 6B is a figure showing a relationship between a measured impedance value and a power value obtained from output high frequency energy. Here, a solid line represents characteristics which are normally set, and a dashed line represents characteristics which are set to a low output.

Discharge is less likely to occur when the output of high frequency energy becomes a certain value or less. As a result of measurement, it was found that when the output was 15 W or less, the discharge did not occur in the present configuration.

In the output control method, as shown in FIG. 6B, the output of high frequency energy is set to 15 W or less during a return period T6 in which the output is low after detection of the abnormality signal. After the return period T6 has elapsed, the system control unit 8 transmits a high frequency energy control signal to the high frequency energy control unit 4*b* and returns the high frequency energy S2 to an original output value (steady-state output setting). The return period T6 in which the low output is obtained can be appropriately set to the time longer than the time during which the abnormality detection signal is output.

Therefore, according to the output control method, even if the abnormality signal is detected, the treatment is continued by reducing the output value without stopping (interrupting) the output of the high frequency energy. Therefore, since the occurrence of discharge can be suppressed and the treatment can also be continued, the operator can continue the treatment without feeling uncomfortable.

[Sixth Output Control Method]

Figure 7A:
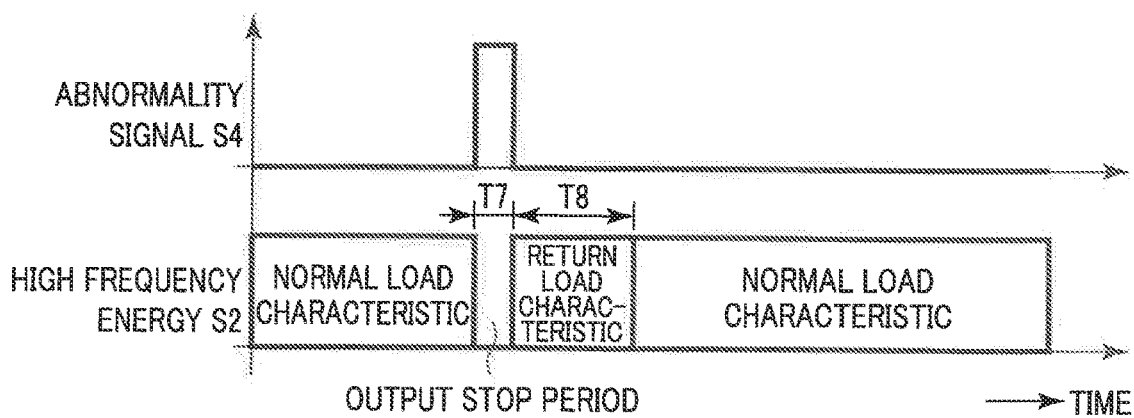
FIG. 7A is a timing chart for explaining a sixth output control method.
Figure 7B:
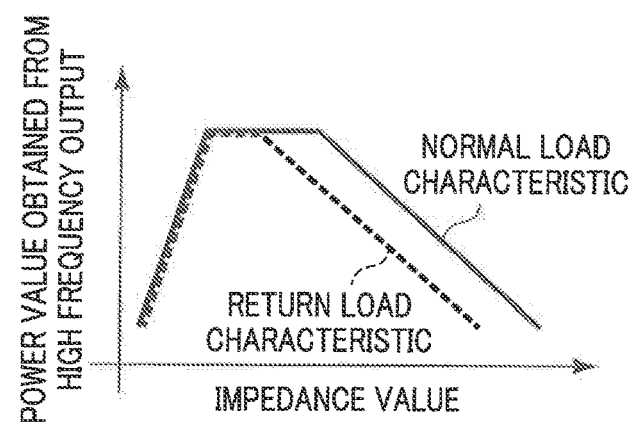
FIG. 7B is a figure showing a first return load characteristic.
Figure 7C:
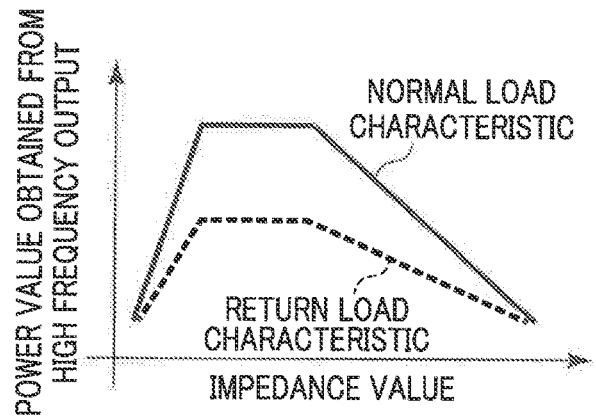
FIG. 7C is a figure showing a second return load characteristic.

Next, a sixth output control method when high frequency energy in the energy treatment system is excessive will be described with reference to a timing chart shown in FIG. 7A. FIG. 7B is a figure showing a first return load characteristic in a relationship between an impedance value and a power value obtained from high frequency energy. Similarly, FIG. 7C is a figure showing a second return load characteristic. Here, in FIGS. 7B and 7C, a solid line represents a normal load characteristic, and a dashed line represents a return load characteristic.

In the sixth output control method, when returning high frequency energy S2 to an original output value, a return load characteristic is provided in advance. The return load characteristic shown in FIG. 7B is set so as to have a low voltage limit. The return load characteristic shown in FIG. 7C is set so as to have a lower power limit than the steady-state load characteristic.

As in the first output control method described above, the energy treatment instrument 10 simultaneously outputs high frequency energy S2 and ultrasonic energy S3 in a state of the stead-state load characteristic, so that the treatment of the treatment subject is performed. According to the progress of the treatment, a fat tissue included in a treatment subject site is generated in the form of mist in the vicinity of the probe 11, as described above.

When the excessive output detection unit 5 detects the excessive output of the high frequency energy S2 during the treatment and the abnormality signal S4 is input to system control unit 8, the high frequency energy control unit 4b stops the output of the high frequency energy S2 during a predetermined interruption period T7 according to the instruction of the system control unit 8.

As the interruption period T7 ends, the system control unit 8 transmits a high frequency energy control signal to the high frequency energy control unit 4b and returns the high frequency energy S2 to an original output value. When returning the output value, the system control unit 8 first switches to a predetermined return load characteristic as shown in FIG. 7B or FIG. 7C. After the switching, the high frequency energy S2 generated by the return load characteristic is output from the energy treatment instrument 10 during a predetermined return period T8.

After the return period T8 has elapsed, the system control unit 8 switches so as to return the steady-state load characteristic to generate the high frequency energy S2, and simultaneously outputs the high frequency energy S2 and the ultrasonic energy S3 from the energy treatment instrument 10.

According to the output control method, in addition to the effect of preventing the occurrence of the discharge by the first output control method described above, the discharge is less likely to occur, as compared with the output at the time of the normal load characteristic, by performing setting to switch to the return load characteristic when returning from the stop of output of the high frequency energy S2 to the original output value. Since the treatment can be continued while ensuring the minimum incision performance, the operator can continue the treatment without feeling uncomfortable.

[Seventh Output Control Method]

Figure 8A:
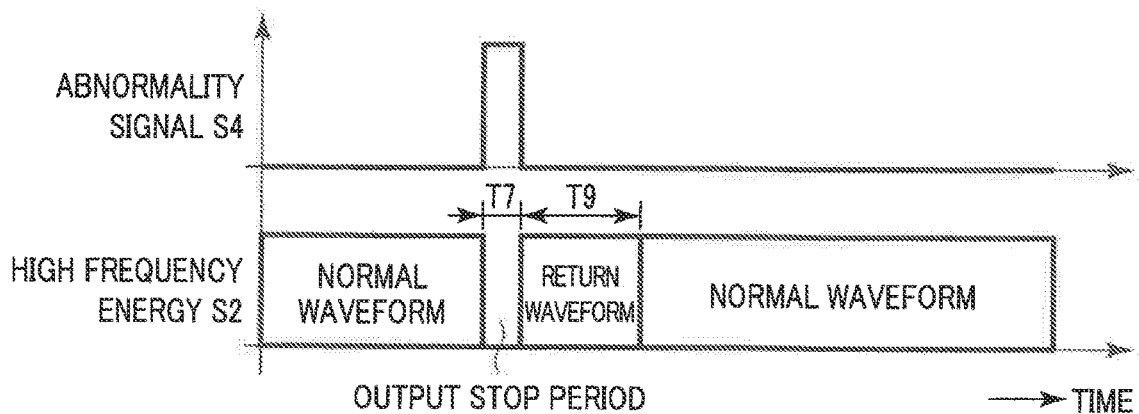
FIG. 8A is a timing chart for explaining a seventh output control method.
Figure 8B:
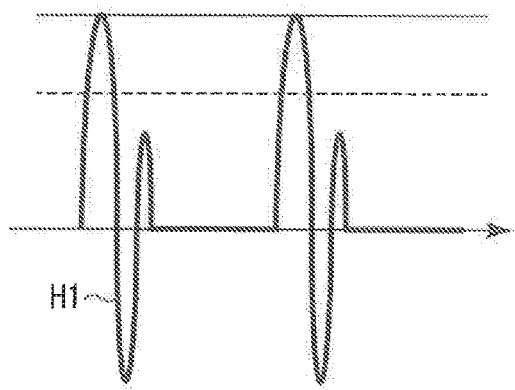
FIG. 8B is a figure showing a steady-state waveform of output high frequency energy.

Next, a seventh output control method when high frequency energy in the energy treatment system is excessive will be described with reference to a timing chart shown in FIG. 8A. FIG. 8B is a figure showing a normal waveform of output high frequency energy. Similarly, FIG. 8C is a figure showing a return waveform of output high frequency energy.

Figure 8C:
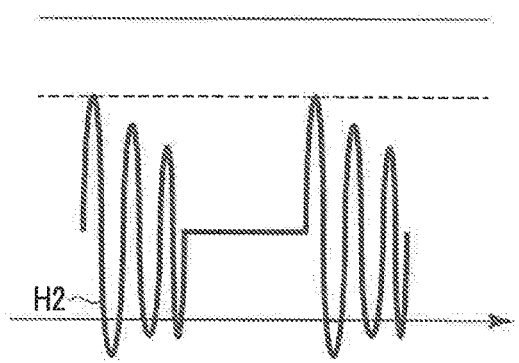
FIG. 8C is a figure showing a return waveform of output high frequency energy.

The seventh output control method is a method which, when returning high frequency energy S2 to an original output value, switches to a return waveform H2 shown in FIG. 8C in which an amplitude (peak value) of a first wave is smaller than a steady-state waveform H1 shown in FIG. 8B and outputs the same.

As in the first output control method described above, the energy treatment instrument 10 simultaneously outputs high frequency energy S2 and ultrasonic energy S3 of the steady-state waveform H1, so that the treatment of the treatment subject is performed. According to the progress of the treatment, a fat tissue included in a treatment subject site is generated in the form of mist in the vicinity of the probe 11.

When the excessive output detection unit 5 detects the excessive output of the high frequency energy S2 during the treatment and the abnormality signal S4 is input to system control unit 8, the high frequency energy control unit 4b stops the output of the high frequency energy S2 during a predetermined interruption period T7. During the interruption period T7, the output of the ultrasonic energy S3 is continued.

As the interruption period T7 ends, the system control unit 8 transmits a high frequency energy control signal to the high frequency energy control unit 4b and returns the high frequency energy S2 to an original output value. When returning the output value, the system control unit 8 switches the output waveform of the high frequency energy S2 from the normal waveform H1 to the return waveform H2 at the beginning of a predetermined return period T9 and outputs the same. The energy treatment instrument 10 simultaneously outputs the high frequency energy S2 and the ultrasonic energy S3 of the return waveform H2.

After the return period T9 has elapsed, the system control unit 8 switches so as to return the steady-state waveform H1 to generate the high frequency energy S2, and simultaneously outputs the high frequency energy S2 and the ultrasonic energy S3 from the energy treatment instrument 10.

According to the output control method, when returning from the stop of the output of the high frequency energy S2 to the original output value, the waveform is switched to the return waveform H2 in which the amplitude (peak value) of the first wave is smaller than the steady-state waveform H1, so that the discharge is less likely to occur. In addition, the treatment can be continued while ensuring the minimum incision performance.

[Eighth Output Control Method]

Figure 9A:
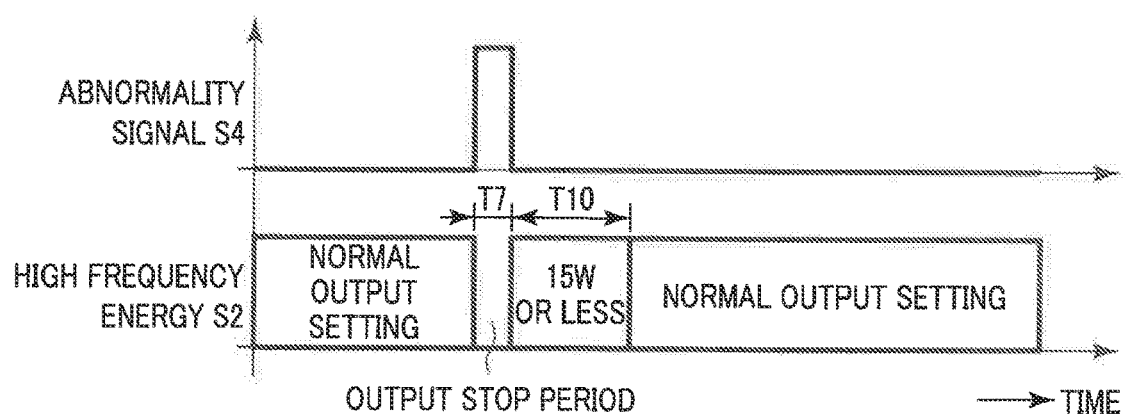
FIG. 9A is a timing chart for explaining an eighth output control method.
Figure 9B:
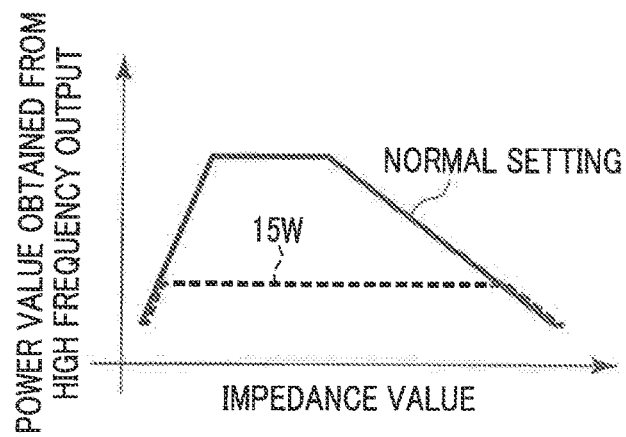
FIG. 9B is a figure showing a return output level characteristic.

Next, an eighth output control method when high frequency energy in the energy treatment system is excessive will be described with reference to a timing chart shown in FIG. 9A. FIG. 9B is a figure showing a return output level characteristic in a relationship between an impedance value and a power value obtained from output high frequency energy.

As in the first output control method described above, the energy treatment instrument 10 simultaneously outputs high frequency energy S2 and ultrasonic energy S3, so that the treatment of the treatment subject is performed. According to the progress of the treatment, a fat tissue included in a treatment subject site is generated in the form of mist in the vicinity of the probe 11.

When the excessive output detection unit 5 detects the excessive output of the high frequency energy S2 during the treatment and the abnormality signal S4 is input to system control unit 8, the high frequency energy control unit 4b stops the output of the high frequency energy S2 during a predetermined interruption period T7 according to the instruction of the system control unit 8. During the interruption period T7, the output of the ultrasonic energy S3 is continued.

As the interruption period T7 ends, the system control unit 8 transmits a high frequency energy control signal to the high frequency energy control unit 4b and returns the high frequency energy S2 to an original output value. When returning the output value, as shown in FIG. 9B, the system control unit 8 outputs the high frequency energy S2 with a return power of 15 W or less during a predetermined return period T10. The high frequency energy S2 returns to the original steady-state output value after the elapse of the return period T10. It can be seen by measurement that the discharge will not occur when the output of the high frequency energy S2 becomes a certain value or less, for example, 15 W or less.

In the output control method, when returning the supply of the high frequency energy S2, once the output is resumed with the output of 15 W or less, the treatment can be continued while ensuring the minimum incision performance. In addition, after the resumption of the supply of the high frequency energy S2, the switching to the steady-state output setting after the preset return period T10 has elapsed makes the discharge less likely to occur. In addition, the operator can continue the treatment without feeling uncomfortable.

In the output control method, the high frequency energy S2 is resumed so as to have the output of 15 W or less. Even if the return power is 15 W or less, the power value set according to the length of the interruption period T7 is different, or the time for which the output can be stopped with the set power value is determined.

In this manner, it is also possible to shorten the interruption period T7 for stopping the output by changing the output value of the high frequency energy S2. In addition, on the contrary, when the interruption period T7 is set to be short, the return power can also be set to be low. In this manner, the interruption period can be set to be shorter according to the level of the return power, and even when the output of the high frequency energy S2 is interrupted with respect to the operator by detecting the abnormality signal, the interruption period can be shortened and the influence on the operator can be minimized.

[Ninth Output Control Method]

Figure 10A:
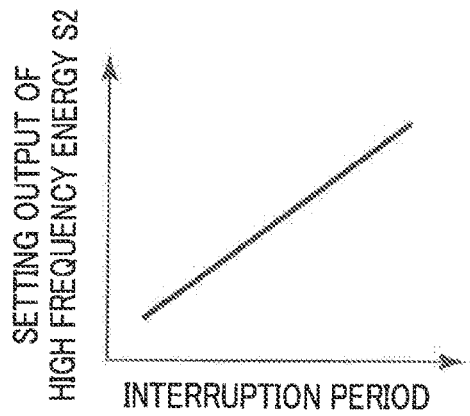
FIG. 10A is a figure showing characteristics of a setting output of high frequency energy with respect to an interruption period as a ninth output control method.
Figure 10B:
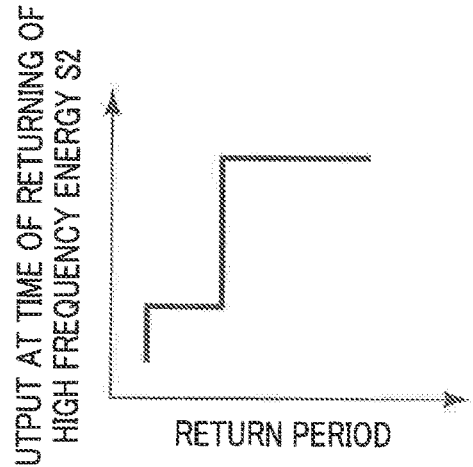
FIG. 10B is a figure showing a relationship between a setting of an output at the time of returning of high frequency energy S2 and an interruption period.
Figure 10C:
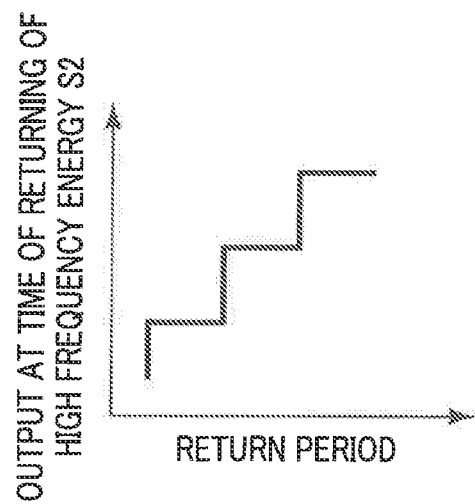
FIG. 10C is a figure showing a relationship between a setting of an output at the time of returning of high frequency energy S2 and an interruption period.

Next, as a ninth output control method of the energy treatment system, an interruption period of high frequency energy and a return period of high frequency energy will be described with reference to FIGS. 10A to 10C. FIG. 10A is a figure showing characteristics of a setting output of high frequency energy S2 with respect to an interruption period. FIGS. 10B and 10C are figures showing a relationship between a setting of an output at the time of returning of high frequency energy S2 and a return period.

As shown in FIG. 10A, the length of the interruption period and the resumption (return) period of the interrupted output of the high frequency energy S2 or the output setting of the high frequency energy S3 at the time of returning are changed according to the magnitude of the excessive power.

FIG. 10B shows a setting state in which the output value in the case of resuming or returning the output of the high frequency energy S2 interrupting the output is increased to the steady-state state in two stages. In the output setting shown in FIG. 10B, when resuming the output of the high frequency energy S2, once an output value smaller than in the steady state is output, it is increased until the output at the steady state after a certain set time. In addition, in the output setting shown in FIG. 10C, when resuming the output of the high frequency energy S2, once an output value smaller than in the steady state is output, it is output so that it reaches a steady-state output value in three stages.

According to the output control method, when returning from the stop of output of the high frequency energy S2 to the original output value according to the magnitude and length of the excessive output, the output value is initially set to be smaller than the steady-state output value, is switched so as to increase stepwise, and is outputted. Therefore, the discharge hardly occurs at the time of returning. In addition, since the interruption period is not unnecessarily prolonged, the operator can continue the treatment without feeling uncomfortable.

According to each control method described above, the interruption period can be shortened by controlling the interruption period of the output or supply of the high frequency energy and the ultrasonic energy and the rise at the time of the output return. Therefore, it is possible to minimize the reduction in incision performance.

[Tenth Output Control Method]

Figure 11:
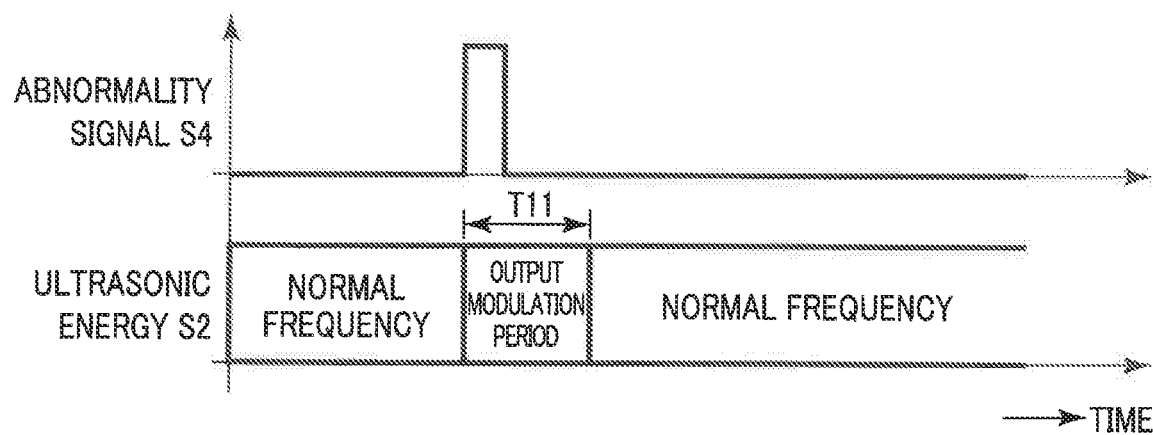
FIG. 11 is a timing chart for explaining a tenth output control method.

Next, a tenth output control method for modulating an output of ultrasonic energy in the energy treatment system will be described with reference to a timing chart shown in FIG. 11. The output control method can also be applied to the sixth to ninth output control methods described above.

The node of the amplitude (waveform) of the ultrasonic vibration in the ultrasonic energy are set, for example, such that the maximum amplitude comes at the probe tip of the probe 11 shown in FIG. 1, whereby the ultrasonic vibration efficiently acts on the incision treatment. The occurrence of mist is suppressed by modulating the frequency of ultrasonic vibration so that the amplitude decreases at the tip of the probe.

As in the first output control method described above, the energy treatment instrument 10 simultaneously outputs high frequency energy S2 and ultrasonic energy S3, so that the treatment of the treatment subject is performed. According to the progress of the treatment, a fat tissue included in a treatment subject site is generated in the form of mist in the vicinity of the probe 11.

When the excessive output detection unit 5 detects the excessive output of the high frequency energy S2 during the treatment and the abnormality signal S4 is input to system control unit 8, the high frequency energy control unit 4b stops the output of the high frequency energy S2 during a predetermined output modulation period T11, as described above with reference to FIG. 2. At the same time, the ultrasonic energy control unit 4a performs modulation so that the amplitude of the ultrasonic vibration is reduced at the tip of the probe. This modulation suppresses the generation of new mist.

As the output modulation period T11 ends, the system control unit 8 transmits a high frequency energy control signal to the high frequency energy control unit 4b and returns the high frequency energy S2 to an original output value. Next, the system control unit 8 transmits an ultrasonic energy control signal to the ultrasonic energy control unit 4a, and returns the ultrasonic energy S3 to an original ultrasonic vibration.

According to the output control method, the occurrence of mist can be reduced by modulating the ultrasonic vibration of the ultrasonic energy and moving so that the node comes at the tip of the probe, it is possible to shorten the time required for searching a resonance point at the time of returning from the ultrasonic wave, and it can be treated at a normal frequency without any discomfort. In the above-described output control method, the return load characteristic and the high frequency energy include changing the parameter according to the connected device, the treatment impedance when or immediately before the output is stopped, and the like.

The invention claimed is:

1. An energy treatment system comprising:
   an energy treatment instrument configured to perform treatment on a subject by simultaneously outputting ultrasonic energy and high frequency energy;
   an ultrasonic energy generator configured to supply the ultrasonic energy to the energy treatment instrument;
   a high frequency energy generator configured to supply the high frequency energy to the energy treatment instrument;
   an excessive output detector configured to:
      compare a parameter of an output of the high frequency energy with a reference parameter of the output of the high frequency energy in a case of not being in an abnormal state,
      detect whether the output of the high frequency energy is an excessive output, and
      output an abnormality signal when the excessive output is detected;
   a high frequency energy controller configured to stop the output of the high frequency energy at a steady state for a preset period when the abnormality signal is outputted by the excessive output detector; and an ultrasonic energy controller configured to:
> increase an output of the ultrasonic energy to be more than the output of the ultrasonic energy in the steady state for the preset period when the abnormality signal is output by the excessive output detector, and
> decrease the output of the ultrasonic energy when the high frequency energy generator resumes the output of the high frequency energy after the abnormality signal is output by the excessive output detector.

2. The energy treatment system according to claim 1, wherein the reference parameter is a parameter acquired under a condition in which discharge does not occur.

3. The energy treatment system according to claim 1, further comprising a system controller configured to control the output of the high frequency energy during a return period after the preset period.

4. The energy treatment system according to claim 3, wherein the system controller is configured to decrease the output of the ultrasonic energy to a normal output when the high frequency energy generator resumes output of the high frequency energy after the abnormality signal is output by the excessive output detector.

5. The energy treatment system according to claim 3, wherein the system controller is configured to gradually or linearly increase a rise of the output of the high frequency energy when resuming the output of the high frequency energy during the return period.

6. A method of operating an energy generation apparatus, the method comprising:
> supplying, by an ultrasonic energy generator, ultrasonic energy to an energy treatment instrument; and
> supplying, by a high frequency energy generator, high frequency energy to the energy treatment instrument;
> wherein the energy generation apparatus further comprises:
>> an excessive output detector configured to:
>>> determine whether an output of high frequency energy is an excessive output by comparing a parameter of the output of the high frequency energy with a reference parameter of the output of the high frequency energy in a case of not being in an abnormal state, and
>>> output an abnormality signal when the excessive output is detected;
>> a high frequency energy controller configured to stop the output of the high frequency energy at a steady state for a preset period when the abnormality signal is outputted by the excessive output detector; and
>> an ultrasonic energy controller configured to:
>>> increase an output of the ultrasonic energy to be more than the output of the ultrasonic energy in the steady state for the preset period when the abnormality signal is output by the excessive output detector, and
>>> decrease the output of the ultrasonic energy when the high frequency energy generator resumes the output of the high frequency energy after the abnormality signal is output by the excessive output detector.

7. The method according to claim 6, wherein the reference parameter is a parameter acquired under a condition in which discharge does not occur.

8. The method according to claim 6, wherein the energy generation apparatus further comprises a system controller configured to control the output of the high frequency energy during a return period after the preset period.

9. The method according to claim 8, wherein the system controller is configured to make a different response to an abnormality signal generated by the excessive output detector when the high frequency energy generator resumes the output of the high frequency energy during the return period.

10. The method according to claim 8, wherein the system controller is configured to gradually or linearly increase a rise of the output of the high frequency energy when resuming the output of the high frequency energy during the return period.

11. An energy generation apparatus connectable with an energy treatment instrument configured to treat a subject by simultaneously outputting ultrasonic energy and high frequency energy, the energy generation apparatus comprising:
> an ultrasonic energy generator configured to supply the ultrasonic energy to the energy treatment instrument;
> a high frequency energy generator configured to supply the high frequency energy to the energy treatment instrument;
> an excessive output detector configured to:
>> compare a parameter of an output of the high frequency energy with a reference parameter of an output of the high frequency energy in a case of not being in an abnormal state,
>> detect whether the output of the high frequency energy is an excessive output, and
>> output an abnormality signal when the excessive output is detected;
> a high frequency energy controller configured to stop the output of the high frequency energy at a steady state for a preset period when the abnormality signal is outputted by the excessive output detector; and
> an ultrasonic energy controller configured to:
>> increase an output of the ultrasonic energy to be more than the output of the ultrasonic energy in the steady state for the preset period when the abnormality signal is output by the excessive output detector, and
>> decrease the output of the ultrasonic energy when the high frequency energy generator resumes the output of the high frequency energy after the abnormality signal is output by the excessive output detector.

12. The energy generation apparatus according to claim 11, further comprising a system controller configured to control the output of the high frequency energy during a return period after the preset period.

13. The energy generation apparatus according to claim 12, wherein the system controller is configured to make a different response to an abnormality signal generated by the excessive output detector when the high frequency energy generator resumes output of the high frequency energy during the return period.

* * * * *